(12) United States Patent
Di Perna et al.

(10) Patent No.: US 9,995,720 B2
(45) Date of Patent: Jun. 12, 2018

(54) PLUG-IN NOX SENSOR SNORKEL FOR READING OPTIMIZATION UNDER PACKAGING CONSTRAINTS

(71) Applicant: GM Global Technology Operations LLC, Detroit, MI (US)

(72) Inventors: Luciano Nunziato Di Perna, Troy, MI (US); Chijou Wang, Farmington Hills, MI (US); Rahul Mital, Rochester Hills, MI (US); Jianwen Li, Farmington Hills, MI (US); James B. Rodgers, Clarkston, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 415 days.

(21) Appl. No.: 14/722,466

(22) Filed: May 27, 2015

(65) Prior Publication Data
US 2016/0349227 A1    Dec. 1, 2016

(51) Int. Cl.
*G01N 33/00* (2006.01)
*F01N 13/00* (2010.01)

(52) U.S. Cl.
CPC ....... *G01N 33/0037* (2013.01); *F01N 13/008* (2013.01); *F01N 2240/20* (2013.01); *F01N 2560/026* (2013.01); *Y02A 50/245* (2018.01)

(58) Field of Classification Search
CPC ............... G01N 33/0037; F01N 13/008
USPC .............................................. 73/23.31
See application file for complete search history.

(56) References Cited

U.S. PATENT DOCUMENTS

| | | | |
|---|---|---|---|
| 2007/0204597 A1* | 9/2007 | Nakano | F01N 3/021 60/276 |
| 2015/0020574 A1* | 1/2015 | Motomura | G01N 15/0656 73/23.31 |
| 2016/0011159 A1* | 1/2016 | Sekiya | G01N 27/4077 73/23.31 |
| 2016/0054182 A1* | 2/2016 | Yoshida | G01K 7/22 374/185 |

* cited by examiner

*Primary Examiner* — Hezron E Williams
*Assistant Examiner* — Tarun Sinha
(74) *Attorney, Agent, or Firm* — Lorenz & Kopf, LLP

(57) ABSTRACT

A snorkel assembly for reading optimization of a sensor, wherein the snorkel assembly may be configured to be positioned around and spaced apart from the sensor. The snorkel assembly may include an upstream side and a downstream side. The snorkel assembly may include a cup section and a tube section extending from the cup section. The tube section may include an inlet opening on the upstream side of the snorkel assembly. The cup section may include an exhaust opening on the downstream side of the snorkel assembly.

20 Claims, 2 Drawing Sheets

PLUG-IN NOX SENSOR SNORKEL FOR READING OPTIMIZATION UNDER PACKAGING CONSTRAINTS

TECHNICAL FIELD

The field to which the disclosure generally relates includes sensing assemblies and more particularly, includes vehicle exhaust system NOx sensor installation assemblies.

BACKGROUND

Frequently, there is a need or desire to sample and analyze a fluid stream contained in a conduit. One such example may involve vehicle exhaust systems wherein an engine's combustion air outflow is conveyed through the exhaust system. A sensor or sensors may be employed in the exhaust system to monitor the level of NOx, which is a generic term for the oxides of nitrogen. NOx may be produced during combustion from a reaction of the natural nitrogen and oxygen that exists in atmospheric air.

SUMMARY OF ILLUSTRATIVE VARIATIONS

A number of illustrative variations may include a snorkel assembly for reading optimization of a sensor, wherein the snorkel assembly may be configured to be positioned around and spaced apart from the sensor. The snorkel assembly may include an upstream side and a downstream side. The snorkel assembly may include a cup section with a tube section extending from the cup section. The tube section may include an inlet opening on the upstream side of the snorkel assembly. The cup section may include an exhaust opening on the downstream side of the snorkel assembly.

Other illustrative variations within the scope of the invention will become apparent from the detailed description provided hereinafter. It should be understood that the detailed description and specific examples, while disclosing variations within the scope of the invention, are intended for purposes of illustration only and are not intended to limit the scope of the invention.

BRIEF DESCRIPTION OF THE DRAWINGS

Select examples of variations within the scope of the invention will become more fully understood from the detailed description and the accompanying drawings, wherein.

DETAILED DESCRIPTION OF ILLUSTRATIVE VARIATIONS

The following description of the variations is merely illustrative in nature and is in no way intended to limit the scope of the invention, its application, or uses.

Figure 1:
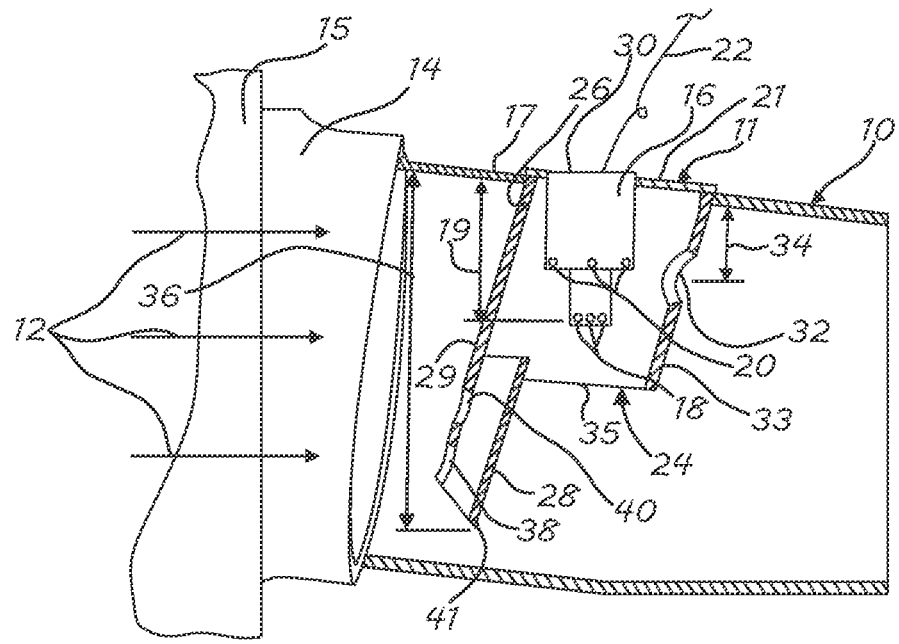
FIG. 1 is a fragmentary, partial cross sectional illustration of an exhaust system with a sensing assembly according to a number of variations.

A variety of systems that involve the flow of fluids may include the measurement, sampling, or sensing of characteristics of the flowing fluid. One such system as illustrated in FIG. 1 may, according to a number of variations, include a conduit in the form of an exhaust pipe 10. The illustrated segment of the exhaust pipe 10 may be interconnected in the exhaust system of a vehicle leading from an internal combustion engine to atmosphere. An exhaust gas stream 12 may be directed out of a selective catalytic reduction unit 15 into the exhaust pipe 10 at a collar 14. The collar 14 may be directly connected to the selective catalytic reduction unit 15. Accurate measurement of the constituents of the fluid stream 12 may be desirable at this location and so a sensing assembly 11 with a sensor 16 may be associated with the exhaust pipe 10. The sensor 16 may be connected to the wall 17 of the exhaust pipe 10 such as by a cover 21 through which it may be inserted and whereby it may extend into the exhaust pipe 10 a distance 19. The sensor 16 may be of a known type that may include inlet ports 18 through which fluid in the exhaust pipe 10 may enter the sensor 16 and may include outlet ports 20 through which fluid may exit the sensor 16 to rejoin the exhaust gas stream 12. Inside the sensor 16, devices may be provided that evaluate the exhaust gas. One such device may be a NOx sensor which may be designed to operate in a high temperature environment and to detect the level of NOx in the exhaust gas stream 12. The sensor 16 may be interconnected with an on-board controller through a conductor bundle 22 to provide feedback control through which operation of the engine and its associated hardware may be varied in response to the sensed NOx level.

The inlet ports 18 may be located approximately at the distance 19 from the wall 17. The homogeneity of the exhaust gas stream 12 may vary over the cross section of the exhaust gas pipe 10, particularly due to the adjacent selective catalytic reduction unit 15 at the collar 14. To assist in providing an accurate sampling of the exhaust gas stream 12, the sensing assembly 11 may be provided with a snorkel assembly 24. The snorkel assembly 24 may include a cup section 26 and a tube section 28. The cup section 26 may generally be of a cylindrical shape and may include an end 30 connected to the wall 17. The cup section 26 may surround the sensor 16 and may include an exhaust opening 32 located on a downstream side 33 at a distance 34 from the wall 17 that may be in line with the outlet ports 20 of the sensor 16, which may also be located approximately at the distance 34 from the wall 17. The tube section 28 may be formed with or connected to the cup section 26 at an upstream side 29 of the snorkel assembly 24. The end 35 of the cup section 26 opposite the end 30 may be open to the exhaust gas stream 12 around the tube section 28. The end 30 may be connected to the wall 17 separately from the sensor 16 so that the exhaust pipe 10 may be fabricated with the snorkel assembly 24 for later addition of the sensor 16. The tube section 28 may extend into the exhaust pipe 10 a distance 36 that is a majority of the distance across the exhaust pipe 10. For example, the distance 36 may be 45 to 55 millimeters in a 60 millimeter diameter exhaust pipe 10. The tube section 28 may have a number of inlet slot openings 38 and 40 distributed along its length and positioned on the upstream side 29 of the tube section 28. The number of inlet openings may be determined by the application and the diameter of the conduit involved to provide multiple separate ports sufficient to capture fluid over a range of the conduit's cross section. In addition, the end 41 of the tube section 26 may be open to the exhaust gas stream 12.

Exhaust gas may enter the snorkel assembly 24 through the inlet slot openings 38 and 40, the end 41 and also through the open end 35 of the cup section 26. These entry points provide a variety of sampling locations from the exhaust gas stream 12 ensuring that an accurate sample of the entire stream is directed into the snorkel assembly 24. Inside the snorkel assembly 24, the exhaust gas may be mixed and a sample of the entrained gas may enter the sensor 16 through the inlet ports 18. Within the sensor 16 the sample may be analyzed and may then exit through the outlet ports 20 and proceed through the exhaust opening 32. Flow must pass into the snorkel assembly 24 to reach the sensor 16.

Figure 2:
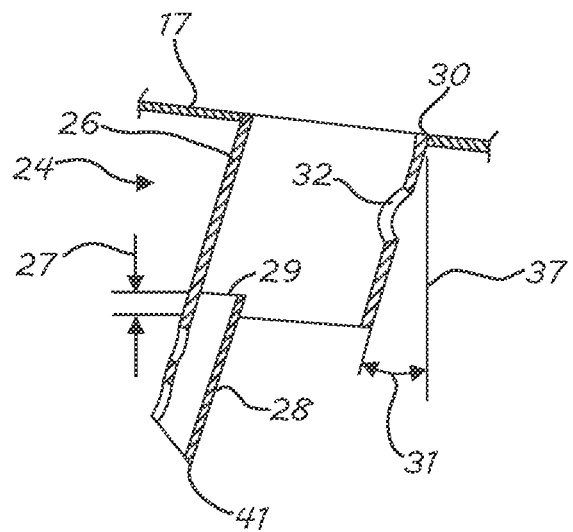
FIG. 2 is a detail cross sectional view of a snorkel assembly for the sensing assembly of FIG. 1.
Figure 3:
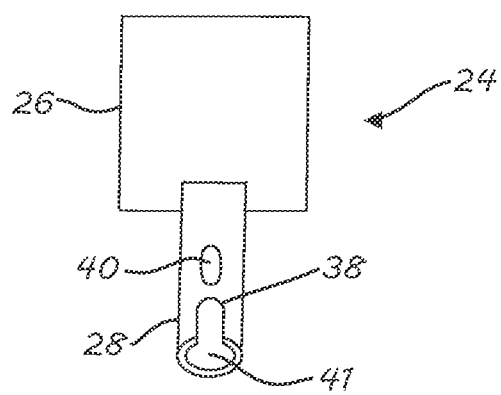
FIG. 3 is a detail view of a snorkel assembly for the sensing assembly of FIG. 1, viewed from an upstream direction.

Referring to FIG. 2, the snorkel assembly 24 is shown in cross section. The tube section 28 may extend into the cylindrical cup section 26 a distance 27 and may terminate at an end 29 that may be below (as viewed in FIG. 2), the exhaust opening 32. This may direct flow toward the sensor 16. The cup section 26 and the tube section 28 are oriented at an angle 31 relative to the exhaust gas stream 12 so that the end 41 meets the exhaust gas stream 12 at an attack angle. The angle 31 may preferably be such that the snorkel assembly 24 is disposed between 7 degrees and 12 degrees relative to a line 37 perpendicular to the fluid stream 12. Providing the angle 31 between 7 and 12 degrees may assist in providing a mixed flow through the snorkel assembly 24 to the sensor 16. In addition, the end 41 is angled to provide an elliptical opening facing the exhaust gas flow 12, which can best be seen in FIG. 3, and so reference is directed thereto. The open end 41 may be formed contiguous with the inlet slot opening 38. As can be seen, the inlet slot openings 38 and 40 may be slot-like and may extend along a length of the tube section 28 to capture a broader section of the exhaust gas stream 12.

Figure 4:
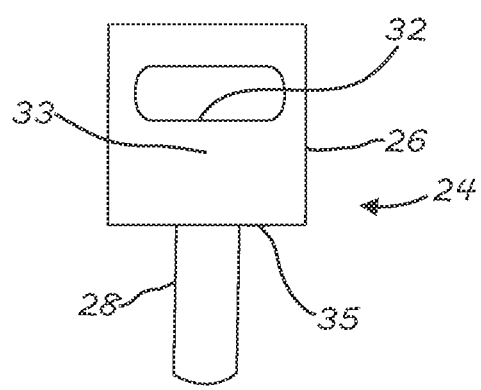
FIG. 4 is a detail view of a snorkel assembly for the sensing assembly of FIG. 1, viewed from a downstream direction.
Figure 5:
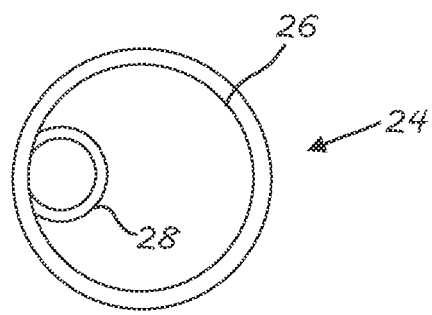
FIG. 5 is a detail view of a snorkel assembly for the sensing assembly of FIG. 1, viewed from an end located adjacent an associated conduit's perimeter wall.

A number of variations may be shown in FIG. 4 which is viewed from the downstream side 33 of the snorkel assembly 24. The exhaust opening 32 may be formed in an extended slot-like shape extending across a part of the cup section 26 and around a part of the cylindrically shaped wall. With reference to FIG. 5 the snorkel assembly 24 is shown from the perspective of the wall 17 where it can be seen that the opposite end 35 of the cup section 26 and the end 41 of the tube section 28 are open. The cup section 26 and the tube section 28 may be formed from tubular sections connected together or may be formed as one piece. The diameter of the cup section 26 may be sized to receive the sensor 16 with sufficient open space for flow mixing. The diameter of the tube section 28 may be substantially smaller than the diameter of the cup section 26 so that flow entrained in the snorkel assembly 24 may slow when entering the cup section 26. The diameter of the tube section may be smaller than the sensor 16.

According to the variations described in relation to FIGS. 1-5, a sensing assembly 11 may provide a mechanism for obtaining an accurate sample of the exhaust gas stream 12. The snorkel assembly 24 may be adapted to receive commercially available NOx sensors. The following description of variants is only illustrative of components, elements, acts, product and methods considered to be within the scope of the invention and are not in any way intended to limit such scope by what is specifically disclosed or not expressly set forth. The components, elements, acts, product and methods as described herein may be combined and rearranged other than as expressly described herein and still are considered to be within the scope of the invention.

Variation 1 may include a snorkel assembly for reading optimization of a sensor, wherein the snorkel assembly may be positioned around and spaced apart from the sensor. The snorkel assembly may include an upstream side and a downstream side. The snorkel assembly may include a cup section and a tube section extending from the cup section. The tube section may include an inlet opening on the upstream side of the snorkel assembly. The cup section may include an exhaust opening on the downstream side of the snorkel assembly.

Variation 2 may include the snorkel assembly according to variation 1 wherein the inlet opening may be comprised of multiple separate ports disposed along the tube section.

Variation 3 may include the snorkel assembly according to variation 1 or 2 wherein the cup section may be cylindrical in shape and the tube section may extend into the cup section.

Variation 4 may include the snorkel assembly according to any of variations 1 through 3 wherein the sensor may include an inlet port and an outlet port and may be configured so that fluid may flow through the sensor.

Variation 5 may include the snorkel assembly according to any of variations 1 through 4 wherein the snorkel assembly is disposed in a fluid stream and may be inclined toward the upstream side at an angle of at least seven degrees relative to a line perpendicular to the fluid stream.

Variation 6 may include the snorkel assembly according to variation 5 wherein the snorkel assembly may be disposed in a conduit carrying an exhaust gas stream.

Variation 7 may include the snorkel assembly according to variation 6 wherein the snorkel assembly may extend across at least seventy-five percent of the conduit's diameter.

Variation 8 may include the snorkel assembly according to variation 1 wherein the cup section may be cylindrical in shape and the exhaust opening may be elongated and may extend around a part of the cup section. The sensor may include an outlet port that may be aligned with the exhaust opening.

Variation 9 may include the snorkel assembly according to variation 1 wherein the tube section may be cylindrical in shape and may include a number of elongated inlet slot openings disposed along the tube section.

Variation 10 may include a sensing assembly with a sensor disposed in a fluid stream. The sensor may sample the fluid stream. A snorkel assembly may be disposed around the sensor. The snorkel assembly may comprise a cup section that may be cylindrical in shape and may have a first diameter. The first diameter may be sized so that the cup section extends around the sensor. The snorkel assembly may comprise a tube section that may have a second diameter. The tube section may extend away from the sensor and into the fluid stream. The second diameter may be smaller than the first diameter so that the sensor cannot extend into the tube section.

Variation 11 may include the sensing assembly according to variation 10 wherein the fluid stream may flow from an upstream side to a downstream side of the sensing assembly. The tube section may include an inlet opening on the upstream side of the snorkel assembly and the cup section may include an exhaust opening on the downstream side of the snorkel assembly.

Variation 12 may include the sensing assembly according to variation 10 or 11 wherein the sensor may include inlet ports and outlet ports. A part of the fluid stream may flow through the sensor.

Variation 13 may include the sensing assembly according to any of variations 10 through 12 wherein the snorkel assembly may be inclined toward the upstream side at an angle of at least seven degrees relative to a line perpendicular to the fluid stream.

Variation 14 may include the sensing assembly according to any of variations 10 through 13 wherein the fluid stream may be an exhaust gas stream carrying a combustion gas.

Variation 15 may include the sensing assembly according to any of variations 10 through 14 wherein the cup section may be cylindrical in shape and may include an elongated exhaust opening extending through the cup section. The sensor may include outlet ports that are aligned with the exhaust opening.

Variation 16 may include the sensing assembly according to any of variations 10 through 15 wherein the tube section may be cylindrical in shape and may include a number of elongated inlet slot openings disposed along the tube section.

Variation 17 may include a sensor assembly with a sensor adapted to measure oxides of nitrogen in a fluid stream. The sensor may extend into an exhaust pipe which may have a wall defining a diameter that contains the fluid stream. The sensor may have an inlet port and an outlet port for admitting a portion of the exhaust stream into and through the sensor. The inlet port and the outlet port may be disposed inside the exhaust pipe. A snorkel assembly may be disposed around the sensor to direct a cross sectional sample of the fluid stream from across the diameter and into the snorkel assembly for delivery to the sensor. The snorkel assembly may extend into the fluid stream a majority of the diameter. The snorkel assembly may have a number of openings distributed across the fluid stream.

Variation 18 may include the sensing assembly according to variation 17 wherein the majority is at least seventy-five percent of the diameter.

Variation 19 may include the sensing assembly according to variation 17 or 18 wherein the snorkel assembly may include a cup section surrounding the sensor and a tube section extending from the cup section in a direction into the fluid stream.

Variation 20 may include the sensing assembly according to any of variations 17 through 19 wherein the snorkel assembly may be inclined into the fluid stream in an upstream direction at an angle of between seven degrees and eleven degrees relative to a line perpendicular to the fluid stream.

The above description of select variations within the scope of the invention is merely illustrative in nature and, thus, variations or variants thereof are not to be regarded as a departure from the spirit and scope of the invention.

What is claimed is:

1. A snorkel assembly for reading optimization of a sensor, the snorkel assembly positioned around and spaced apart from the sensor, the snorkel assembly comprising an upstream side and a downstream side, with a cup section and a tube section extending from the cup section, the cup section having a first diameter and extends to a terminal end and the tube section having a second diameter smaller than the first diameter, the tube section is offset to the upstream side of the snorkel assembly relative to the cup section and extends into the cup section and out of the terminal end, wherein tube section defines an inlet opening on the upstream side of the snorkel assembly and the cup section defines an exhaust opening on the downstream side of the snorkel assembly.

2. The snorkel assembly according to claim 1 wherein the inlet opening is comprised of multiple separate ports disposed along the tube section.

3. The snorkel assembly according to claim 1 wherein the cup section is cylindrical in shape.

4. The snorkel assembly according to claim 1 wherein the sensor includes an inlet port and an outlet port and is configured so that a fluid flows through the sensor from the inlet port to the outlet port, and wherein the inlet port is in the tube section only, and the outlet port is in the cup section only.

5. The snorkel assembly according to claim 1 wherein the snorkel assembly is disposed in a fluid stream and the snorkel assembly is inclined toward the upstream side at an angle of at least seven degrees relative to a line perpendicular to the fluid stream.

6. The snorkel assembly according to claim 5 wherein the snorkel assembly is disposed in a conduit and the fluid stream comprises an exhaust gas stream.

7. The snorkel assembly according to claim 6 wherein the conduit has a wall defining a diameter and the snorkel assembly extends across at least seventy-five percent of the diameter.

8. The snorkel assembly according to claim 1 wherein the cup section is cylindrical in shape and the exhaust opening is elongated around a part of the cup section and the sensor defines an outlet port that is aligned with the exhaust opening.

9. The snorkel assembly according to claim 1 wherein the tube section is cylindrical in shape and wherein the inlet opening is comprised of a plurality of inlet openings disposed along the tube section.

10. A sensing assembly comprising a sensor disposed in a fluid stream, the sensor sampling the fluid stream, a snorkel assembly disposed around the sensor, the snorkel assembly comprising a cup section that is cylindrical in shape and of a first diameter and extends around the sensor, the snorkel assembly comprising a tube section that has a second diameter, the tube section extending away from the sensor and into the fluid stream farther than the cup section, the second diameter smaller than the first diameter wherein the cup section extends into the fluid stream to a first terminal end that is open and the tube section extends out of the first terminal end to a second terminal end that is open.

11. The sensing assembly according to claim 10 wherein the fluid stream flows from an upstream side to a downstream side of the sensing assembly and wherein the tube section defines an inlet opening on the upstream side and the cup section defines an exhaust opening on the downstream side, wherein the snorkel assembly is configured to direct fluid stream first through the tube section and then through the tube section and then through the cup section.

12. The sensing assembly according to claim 11 wherein the sensor includes inlet ports and outlet ports wherein a part of the fluid stream flows through the sensor.

13. The sensing assembly according to claim 12 wherein the snorkel assembly is inclined toward the upstream side at an angle of at least seven degrees relative to a line perpendicular to the fluid stream.

14. The sensing assembly according to claim 13 wherein the fluid stream comprises an exhaust gas stream carrying a combustion gas.

15. The sensing assembly according to claim 10 wherein the cup section is cylindrical in shape and includes an elongated exhaust opening extending through the cup section and the sensor includes outlet ports that are aligned with the exhaust opening.

16. The sensing assembly according to claim 10 wherein the tube section is cylindrical in shape and includes a number of elongated inlet slot openings disposed along the tube section, wherein the cup section is defined by a wall and wherein the tube section is offset relative to the cup section to an upstream side of the snorkel assembly and is aligned with the wall on the upstream side.

17. A sensor assembly comprising a sensor adapted to measure oxides of nitrogen in a fluid stream, the sensor extending into an exhaust pipe that has a wall defining a diameter and containing the fluid stream, the sensor defines an inlet port and an outlet port for admitting a portion of the exhaust stream into and through the sensor, the inlet port and the outlet port disposed inside the exhaust pipe, a snorkel assembly disposed around the sensor to direct a sample of the fluid stream from across the diameter and into the snorkel assembly for delivery to the sensor, the snorkel assembly extending into the fluid stream a majority of the diameter, the snorkel assembly having a number of openings distributed across the fluid stream, wherein the snorkel assembly includes a cup section surrounding the sensor and a tube section extending from the cup section in a direction away from the sensor and into the fluid stream, wherein the cup section extends into the fluid stream to a first terminal end that is open and the tube section extends out of the first terminal end to a second terminal end that is open, wherein the cup section is defined by a wall and wherein the tube section is offset relative to the cup section to an upstream side of the snorkel assembly and is aligned with the wall on the upstream side.

18. The sensor assembly according to claim 17 wherein the majority is at least seventy-five percent of the diameter.

19. The sensor assembly according to claim 17 wherein the tube section extends into the cup section a distance and terminates at a tube end in the cup section wherein the tube end is closer to the first terminal end than the outlet port.

20. The sensor assembly according to claim 17 wherein the snorkel assembly is inclined into the fluid stream in an upstream direction at an angle of between seven degrees and eleven degrees relative to a line perpendicular to the fluid stream.

* * * * *